PEAR TREE AND FRUIT
Filed Aug. 26, 1968
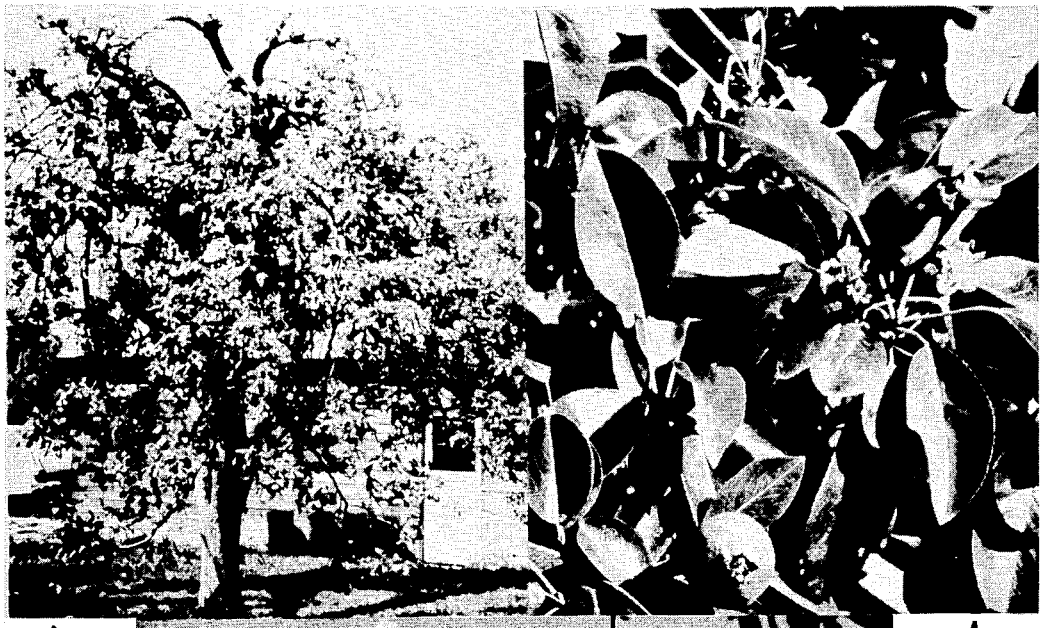
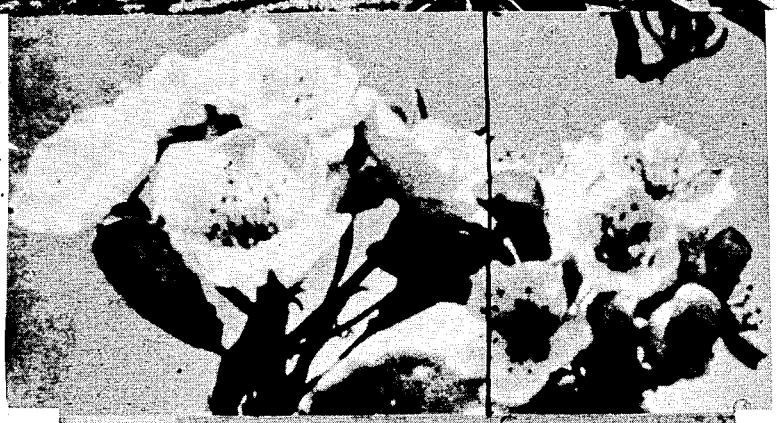
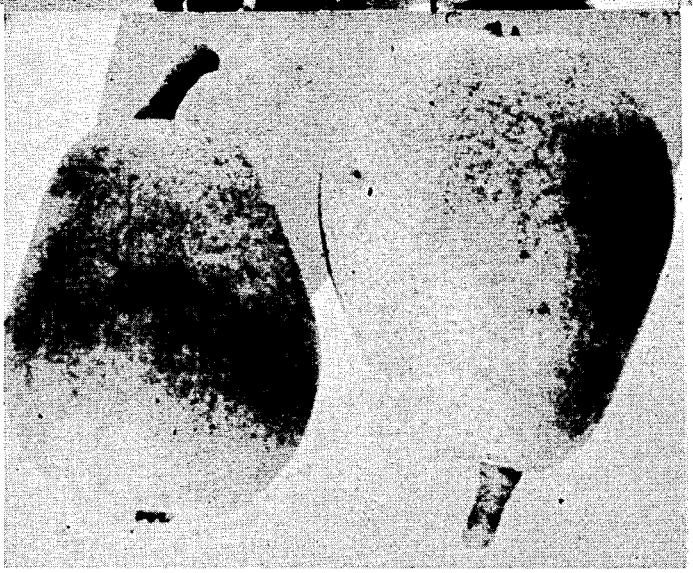
↑ original tree 6/68 Height: 16 ft. Spread: 26 ft.
→ large blossom with double row of petals characteristic of Lady Marion
↑ typical leaf shape with crenate margin
← smaller single blossoms of Bartlett
→ fruit shape typical with short, thick stem, prominent calyx: larger fruit 5 in. from tip of stem to tip of calyx.
Variety Discovered By: Thomas F. Wells

United States Patent Office

Plant Pat. 2,985
Patented July 28, 1970

2,985
PEAR TREE AND FRUIT

Thomas F. Wells, 841 E. 48th, Tacoma, Wash. 98404

Filed Aug. 26, 1968, Ser. No. 755,472
Int. Cl. A01g *5/03*
U.S. Cl. Plt.—36 1 Claim

DESCRIPTION

Originated: 841 E. 48th, Tacoma, Wash. 98404; approximated year 1921 as a seedling.

By whom originated: Unknown.

First propagated by: Thomas F. Wells, January 1968, by root grafting on certified "Old Home" stock (450), and "Quince" (50).

Root stock obtained from: Daybreak Nursery, Rt. 2, Box 96, Cornelius, Oreg.

Inspected: Department of Agriculture, State of Oregon. Washington State Dept. of Agriculture, Olympia, Field Inspector's Receipt 51644.

Not introduced to trade, but named "Lady Marion."

Name and address of present owner: Thomas F. Wells, 841 E. 48th, Tacoma, Wash. 98404.

Specimens described are grown at: 841 E. 48th, Tacoma, Wash. 98404.

Dates of first and last picking: August 10 to August 20 (approximately).

Tree: Medium size, vigorous, upright, spreading, dense, round-top, open center, medium growing, hardy, very productive, regular bearing (yearly).

Trunk: Medium build, medium smooth bark.

Branches:

*Size.*—Medium-thick; smooth; medium-heavy branching. 1st year wood—reddish-brown. 2nd year wood—brownish-grey. 3rd year and older wood—grey.

*Lenticels.*—Medium quantity, not prominent. Size about 1 mm. long, ½ mm. wide, smooth, turn dark and slightly rough on older wood; not conspicuous after four years.

Leaves:

*Length.*—Blades up to 12 cm.

*Width.*—Blades ½ to ⅓ length on new growth (spurs tend to have narrower blades, longer petioles).

*Size.*—Large; width—medium, long, ovate, taper pointed (short), thick, leathery, dark green, very smooth.

*Margins.*—No glands, finely crenate (crenate serrations about 10 per cm).

*Petiole.*—Long, 5 to 8 cm.; slender to medium in size.

Flowers:

*Feb. 20, 1968.*—Buds started to swell (photo).

*Mar. 1, 1968.*—Buds swelled and pointed; larger more pointed than Bartlett.

*Mar. 8, 1968.*—Green bud (¾ to 1 inch scale); leaves recurved.

*Mar. 14, 1968.*—Cluster bud (photo). First bloom from mid-April to about May 10, begins to bloom when Bartlett in full bloom; late compared to others, large, white with pink edges and centers.

*Mar. 18, 1968.*—Buds beginning to spread; sepals longer, pointed over pink bud; Bartlett—shorter, rounded.

*Mar. 22, 1968.*—Bud cluster spreading; 1st stage of pink with calyces not touching over petals on about 20%.

*Mar. 26, 1968.*—May '67 fruiting spurs producing flower buds.

*Mar. 29, 1968.*—Full pink; first leaves unfolding about (2"). Barlett blossoms partly open.

*Apr. 3, 1968.*—About 50% full bloom. Number of petals range from 5 to 10; large, showy; retain slight pink on the edges (photo).

*Apr. 9, 1968.*—Full bloom. Samples sent to New York.[1]

*Apr. 12, 1968.*—Snow.

*Apr. 17, 1968.*—Petal fall about 75%. Young pears reddish, on Bartlett, mostly green. Temperature—12:30 a.m., 32°; 5:30 a.m., 28°.

*May 2, 1968.*—New shoot growth vigorous—about 4", leaves up to double the size of Bartlett leaves—darker green. Non-pollinated fruits dropping; new fruits up to ½" diam. Occasional large, late flowers.

*May 9, 1968.*—Pears almost 1 in.: leaves large, deeper green than Bartlett.

*May 23, 1968.*—Occasional flowers still developing—all doubles; several rows of petals; pears about 1" long, ¾" in diameter; several blossom petals reverted to green leaves.

*May 27, 1968.*—Gathered samples of double flowers and petals and leaves from flower buds. Samples sent to: Robt. C. Lamb, Department of Pomology, Cornell University (see footnote 1).

*June 3, 1968.*—Pears beginning to turn downward.

*June 11, 1968.*—Pears turning downward.

*June 20, 1968.*—Occasional leaf showing slight powdery mildew. (A single psylla, dead; on Bartlett.)

Largest fruits 8.3 cm. long including stem; stem thick, about 2.5 cm. long, fruit about 5 cm.; calyx 8 mm. Largest diameter about 4 cm., 2 cm. from calyx base; calyx open, fruit slightly ridged in line with sepal points.

Fruit: (1967) Maturity when described eating hard over under ripe date (green eating August 15–25).

*Size.*—Variable, axial diam. up to 13 cm.; traverse up to 8 cm.; rounded pyroform slightly flattened at calyx end; some fruits shown slightly depressed calyx.

*Cavity.*—Symmetrical; flattened to slightly depressed; not ridged.

*Basin.*—Symmetrical; occasional small shoulder, slightly oblique; mostly continuous with stem.

Stem: Straight thick; glabrous; slightly russeted, mostly 2 to 2.5 cm. long; up to 10 mm. thick.

Calyx: Open; segments persistent; bace thickened; flare slightly; sepals joined; about 5 mm. long. Both stamen and pistil remnants persist.

Skin: Thick, tender, smotoh, glossy; dots inconspicuous, small numerous, green; irregular round, tiny russet center; ground color slightly yellowish green; blush reddish; bloom scant.

Flesh: Juicy; slightly cream-colored; tender, melting stone cells few, small; flavor mild subacid; delicately rich; quality very good.

Core: Distant; broadly ovate; core lines closed; carpels small, thin-walled; calyx tube closed, pistils persistent.

Seeds: Small number perfect; 2 per cell.

Use: Excellent canned product; good fresh but short period; high sugar; possible dietetic value.

Keeping quality: Medium, about 18 days between harvest and ripening for canning.

Resistance: Good, no particular problem with insects; not susceptible to scab; no pear blight on the original tree; occasional powdery mildew on the new leaves;

[1] Cornell University, New York State Agricultural Experiment Station, Geneva, N.Y. 14456, Dept. of Pomology, Top Work by Robert C. Lamb, Associate Professor.

green aphids usually appear about mid-June; no problem with psylla.

General notes: Compared with Bartlett, shorter storage period before ripening to eat green; superior flesh quality; requires less sugar in canning; flowers large, showy, frequently double; sets fruit every year; seems resistant to spring frosts.

I claim:

1. The new and distinct pear variety to be characterized particularly by:

(a) An unusual blossoming habit, in that flowers frequently produce double and sometimes triple rows of petals.

(b) an apparent resistance to late spring frosts.

(c) a tendency to annual and prolific bearing.

(d) production of fruits larger than those of other varieties of approximately the same season, namely Bartlett.

(e) a shape with distinctively different features for varieties of the same season, particularly as to appearance of the calyx and stem ends.

(f) flesh characters adaptable to processing that may be favorable for persons on low sugar diets.

No references cited.

ROBERT E. BAGWELL, Primary Examiner